US00PP12078P2

(12) United States Plant Patent
Bullis, III

(10) Patent No.: US PP12,078 P2
(45) Date of Patent: Sep. 4, 2001

(54) AECHMEA PLANT NAMED 'LOIE'S PRIDE'

(75) Inventor: Harvey R. Bullis, III, Princeton, FL (US)

(73) Assignee: Bullis Bromeliads, Inc., Princeton, FL (US)

( * ) Notice: Subject to any disclaimer, the term of this patent is extended or adjusted under 35 U.S.C. 154(b) by 0 days.

(21) Appl. No.: 09/639,894

(22) Filed: Aug. 16, 2000

(51) Int. Cl.[7] ..... A01H 5/00
(52) U.S. Cl. ..... Plt./370

(58) Field of Search ..... Plt./370

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Aechmea plant named 'Loie's Pride', characterized by its upright and outwardly arching growth habit; unique green and yellow variegated foliage with green margins and yellow central longitudinal stripes; inflorescences held upright and above foliage on strong red scapes; tightly branched inflorescences with bright yellow and red flower bracts; and long-lasting inflorescences.

1 Drawing Sheet

BACKGROUND OF THE INVENTION

The present Invention relates to a new and distinct cultivar of Aechmea plant, botanically known as *Aechmea chantinii* and referred to by the cultivar name Loie's Pride.

The new Aechmea is a naturally-occurring branch mutation of the *Aechmea chantinii* cultivar Little Harv, not patented. The new Aechmea was discovered and selected by the Inventor within a population of plants of the cultivar Little Harv grown in a controlled environment in Princeton, Fla. in 1987. The new Aechmea was selected based on its unique yellow and green variegated leaves; plants of the cultivar Little Harv have solid green-colored leaves.

Asexual reproduction of the new Aechmea by offsets taken in a controlled environment in Princeton, Fla., has shown that the unique features of this new Aechmea are stable and are reproduced true to type in successive generations.

SUMMARY OF THE INVENTION

The new Aechmea has not been observed under all possible environmental conditions. The phenotype may vary somewhat with variations in environment such as temperature, daylength, light intensity, fertilizer rate and type, and/or irrigation amount and frequency without, however, any variance in genotype.

The following characteristics have been repeatedly observed and are determined to be basic characteristics of 'Loie's Pride' and distinguish 'Loie's Pride' as a new and distinct cultivar:

1. Upright and outwardly arching growth habit.
2. Unique green and yellow variegated foliage with green margins and yellow central longitudinal stripes.
3. Inflorescences held upright and above foliage on strong red scapes.
4. Tightly branched inflorescences with bright yellow and red flower bracts.
5. Long-lasting inflorescences.

Plants of the new Aechmea differ from plants of the cultivar Harvey's Pride, disclosed in the U.S. Plant Patent application Ser. No. 09/639,895, primarily in variegation pattern as leaves of plants of the cultivar Loie's Pride have green margins and yellow centers.

BRIEF DESCRIPTION OF THE PHOTOGRAPHS

The accompanying colored photographs illustrate the overall appearance of the new Aechmea, showing the colors as true as it is reasonably possible to obtain in colored reproductions of this type. Colors in the photographs may differ slightly from the color values cited in the detailed botanical description which more accurately describe the actual colors of the new Aechmea.

The photograph at the top of the sheet comprises a side perspective view of a typical plant of 'Loie's Pride' that was about 12 months old and grown in a 25.5-cm container.

The photograph at the bottom of the sheet comprises a close-up view of typical leaves and a typical inflorescence of 'Loie's Pride'.

DETAILED BOTANICAL DESCRIPTION

The following observations, measurements, values, and comparisons describe plants grown in Princeton, Fla., under a polypropylene-covered shade house and conditions which closely approximate those used in commercial practice. Plants were grown with an average day temperature of 25.5° C. and an average night temperature of 18° C. The polypropylene shadecloth provided a 80 percent decrease in ambient light levels. Single plants used for this description were about 12 months old and grown in 25.5-cm containers. Color references are made to The Royal Horticultural Society Colour Chart except where general terms of ordinary dictionary significance are used.

Botanical classification: *Aechmea chantinii* cultivar Loie's Pride.

Parentage: Naturally-occurring branch sport mutation of *Aechmea chantinii* cultivar Little Harv, not patented.

Propagation:

*Type.*—By offsets.

*Time to initiate roots.*—Summer: About 28 days at temperatures of 29 to 35° C. Winter: About 38 days at temperatures of 18 to 27° C.

*Time to develop roots.*—Summer: About 80 days at temperatures of 29 to 35° C. Winter: About 120 days at temperatures of 18 to 27° C.

*Root description.*—Fine and freely branching.

Plant description:

*General appearance.*—Upright and outwardly arching growth habit. Rosette leaves are erect when young, becoming outwardly arching with development. Appropriate for 25.5-cm containers. Plants readily produce offsets.

*Crop time.*—From offsets, typically about 11 to 14 months are required to produce flowered finished plants in 25.5-cm containers.

*Plant height.*—Soil surface to top of leaf canopy: About 90 cm. Soil surface to top of inflorescence: About 118 cm.

*Plant diameter or spread.*—About 120 cm.

*Growth rate/vigor.*—Vigorous.

*Foliage description.*—Arrangement: Rosette, spiral phyllotaxis. Quantity of leaves per plant: About 38. Shape: Linear. Apex: Cuspidate. Margin: Very sharp spines. Length: About 92 cm. Width: About 9.3 cm. Aspect: Concave. Texture: Leathery, thick; lower surface, glaucous and dull. Color: Young and mature leaves, upper surface: Central longitudinal stripes, between 6C and 6D underlain with close to 147A; margins and parallel longitudinal stripes towards the margins, close to 147A. Young and mature leaves, lower surface: Central longitudinal stripes, between 6C and 6D overlain with close to 147A; margins and parallel longitudinal stripes towards the margins, close to 147A; dulled.

Inflorescence description:

*Inflorescence form.*—Large terminal inflorescences arranged in tightly branched and spirally twisting lateral panicles supported by erect and strong scapes. About 18 lateral panicles each with about 22 individual flowers. Flowers ovoid in shape; bright red and yellow flower bracts.

*Inflorescence longevity.*—Inflorescences of the new Aechmea are very long-lasting; typically bract color will be maintained for about two to four months.

*Inflorescence size.*—Length: About 28 cm. Width: About 13 cm.

*Lateral panicle size.*—Length: About 9.2 cm. Diameter: About 2.4 cm.

*Flower size.*—Length: About 2.4 cm. Diameter: About 8 mm.

*Primary bracts.*—Arrangement: Subtend each trilateral panicle. Shape: Linear. Length: About 11.7 cm. Width: About 3.4 cm. Texture: Glaucous. Color: 46C.

*Flower bracts.*—Arrangement: Closely adhered to sepals. Shape: Elongate, sharply acuminate. Length: About 2.4 cm. Width: About 6 mm. Texture: Smooth. Color: Initially yellow green, 154A, becoming bright yellow, 9A, then bright red, 46C to 46D, starting at the base.

*Petals.*—Appearance: Not united, usually with two scales inside of sepals. Color: White to green, 154A.

*Scape.*—Strength: Very strong. Aspect: Typically erect. Length: About 118 cm. Diameter: About 1.4 cm. Texture: Sticky, glaucous. Color: 46D.

*Seed.*—Seed production has not been observed.

Temperature tolerance: Plants of the new Aechmea tolerate temperatures from 3 to above 41° C.

Disease resistance: Disease resistance to pathogens common to Aechmea has not been documented.

It is claimed:

1. A new and distinct cultivar of Aechmea plant named 'Loie's Pride', as illustrated and described.

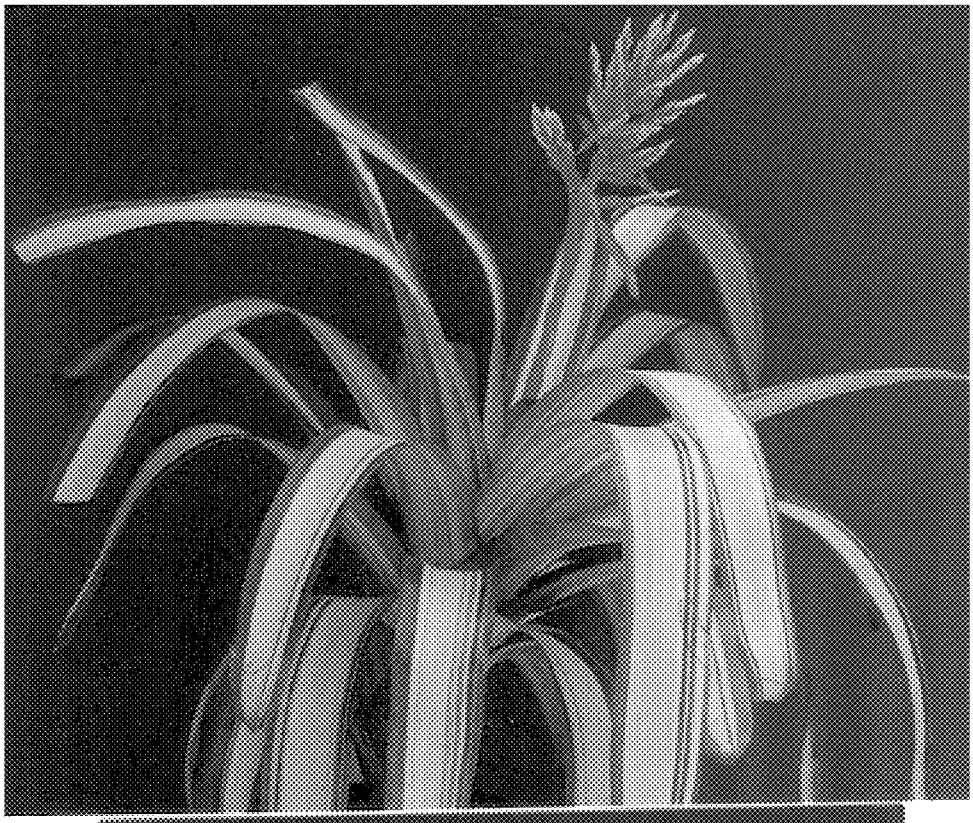
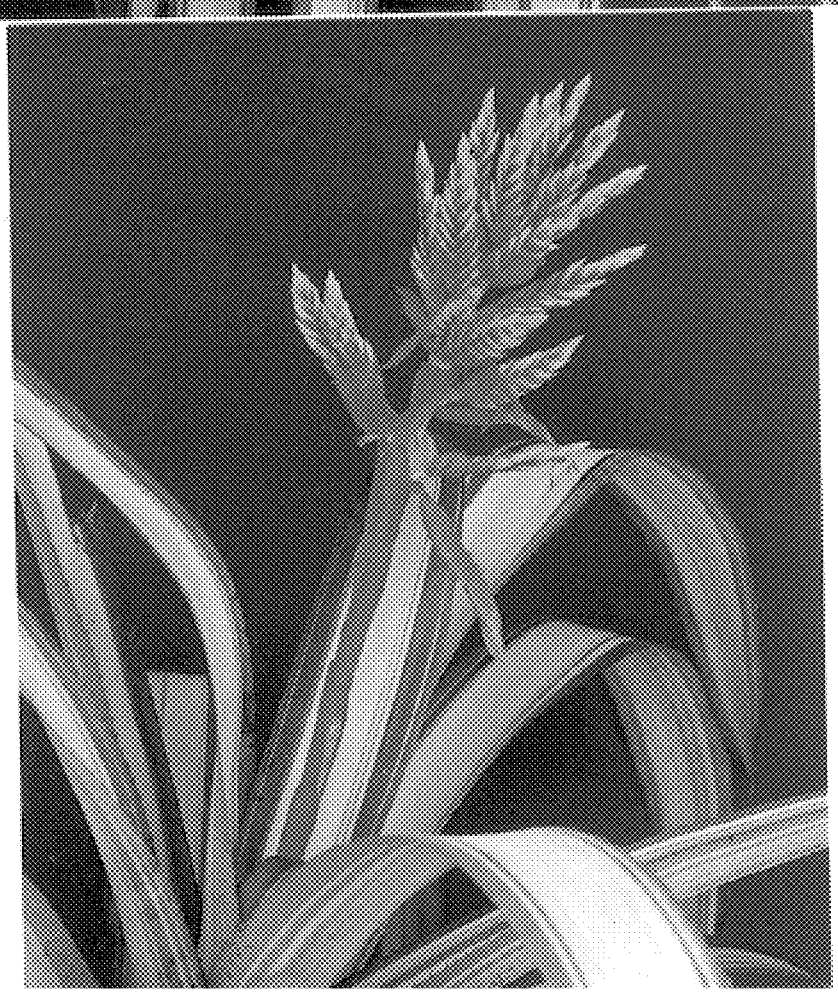

* * * * *